United States Patent [19]

Singer

[11] 4,151,279
[45] Apr. 24, 1979

[54] FUNGICIDAL N-CARBAMYLOXY-2,3-DISUBSTITUTED 4-TRIHALOMETHYL-6-OXOTETRAHYDRO-1,3-OXAZINES

[75] Inventor: Malcolm S. Singer, Novato, Calif.

[73] Assignee: Chevron Research Company, San Francisco, Calif.

[21] Appl. No.: 916,434

[22] Filed: Jun. 19, 1978

[51] Int. Cl.² .................. A61K 31/535; C07D 265/06
[52] U.S. Cl. .......................... 424/248.5; 424/248.55; 544/71; 544/97
[58] Field of Search ............... 544/97, 71; 424/248.5, 424/248.55

[56] References Cited
FOREIGN PATENT DOCUMENTS
230163 10/1968 U.S.S.R. ..................................... 544/97

OTHER PUBLICATIONS
Luknitskii et al., Chem. Abstracts, vol. 69, abst. 2920y, (1968), (Abst. of Khim. Geterotsikl. Soedin, 1967, (5), pp. 954-955).

Primary Examiner—John D. Randolph
Attorney, Agent, or Firm—Dix A. Newell; Thomas G. DeJonghe

[57] ABSTRACT

N-carbamyloxy-6-oxotetrahydro-1,3-oxazines of the formula

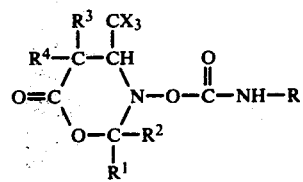

wherein
R is hydrogen, alkyl or aryl,
$R^1$ and $R^2$ are alkyl or aryl,
X is halo,
$R^3$ and $R^4$ are hydrogen, alkyl or halo, with the proviso that two $R^1$ and $R^2$ groups may together form a divalent alkylene group of 3 to 5 carbon atoms, have been found to be excellent plant fungicides, particularly for plant diseases caused by *Phytophthora infestans* and the fungal species of the *Peronosporaceae* family.

11 Claims, No Drawings

FUNGICIDAL N-CARBAMYLOXY-2,3-DISUBSTITUTED 4-TRIHALOMETHYL-6-OXOTETRAHYDRO-1,3-OXAZINES

DESCRIPTION OF THE PRIOR ART

Chem. Abs., Vol. 71, 13119m (1969) discloses the preparation of N-hydroxy-4-trichloromethyl-6-oxotetrahydro-1,3-oxazines by treating beta-(trichloromethyl)-beta-propiolactone with antioximes of aldehydes of oximes of ketones. Chem. Abs., Vol. 69, 2920y (1968) discloses the reaction of beta-(trichloromethyl)-beta-propiolactone and azomethines to produce either 6-oxo- or 4-oxo-tetrahydro-1,3-oxazines.

DESCRIPTION OF THE INVENTION

The N-carbamyloxy-2,2-disubstituted-4-trihalomethyl-6-oxotetrahydro-1,3-oxazines of the invention are represented by the formula (I)

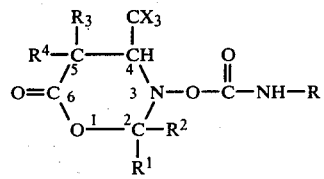

wherein $R^1$ and $R^2$ individually are alkyl of 1 to 6 carbon atoms, phenyl, or phenyl substituted with 1 to 3 of the same or different substituents selected from fluoro, chloro, bromo, iodo, alkyl of 1 to 4 carbon atoms, alkoxy of 1 to 4 carbon atoms or alkylthio of 1 to 6 carbon atoms, X is chloro or bromo, $R^3$ and $R^4$ individually are hydrogen, chloro, bromo or alkyl of 1 to 6 carbon atoms, R is hydrogen, alkyl of 1 to 6 carbon atoms, phenyl, or phenyl substituted with 1 to 3 of the same or different substituents selected from fluoro, chloro, bromo, iodo, alkyl of 1 to 4 carbon atoms, alkoxy of 1 to 4 carbon atoms or alkylthio of 1 to 6 carbon atoms, with the proviso that two $R^1$ and $R^2$ groups may together form a divalent alkylene group of 3 to 5 carbon atoms.

Representative alkyl groups which R, $R^1$, $R^2$, $R^3$ and $R^4$ may represent include methyl, ethyl, isopropyl, t-butyl and hexyl. Representative substituted-phenyl group which R, $R^1$, $R^2$, $R^3$ and $R^4$ may represent include 2-chlorophenyl, 4-fluorophenyl, 3-bromophenyl, 4-iodophenyl, 2,4-dichlorophenyl, 2,4,6-trichlorophenyl, 4-methylphenyl, 2-chloro-4-methylphenyl, 2-methoxyphenyl, 2-methyl-thio-4-methylphenyl, and 4-ethylthiophenyl. Representative divalent alkylene groups formed by joining $R^1$ and $R^2$ include trimethylene, tetramethylene, 2-methyltrimethylene.

Preferably R is phenyl or phenyl substituted with 1 to 2 of the same or different substituents selected from fluoro, chloro, bromo, alkyl of 1 to 4 carbon atoms or alkoxy of 1 to 4 carbon atoms. Most preferably R is phenyl or phenyl substituted with 1 to 2 fluoro, chloro or bromo, especially chloro.

Preferably $R^1$ is alkyl of 1 to 3 carbon atoms, especially methyl.

Preferably $R^2$ is alkyl of 1 to 3 carbon atoms, phenyl or phenyl substituted with 1 to 2 fluoro, chloro or bromo. Most preferably $R^2$ is methyl or phenyl.

Preferably X is chloro.

Preferably $R^3$ and $R^4$ are hydrogen, chloro or bromo. Most preferably both $R^3$ and $R^4$ are hydrogen, or chloro.

Preferred class of compounds represented by formula (I) is that wherein $R^1$ and $R^2$ are alkyl of 1 to 3 carbon atoms or phenyl, X is chloro, both $R^3$ and $R^4$ are hydrogen or chloro and R is phenyl or phenyl substituted with 1 to 2 chloro groups.

Another preferred class is that wherein $R^1$ and $R^2$ together form triemthylene or tetramethylene, X is chloro, both $R^3$ and $R^4$ are hydrogen or chloro, and R is phenyl or phenyl substituted with 1 to 2 chloro groups.

The components of the invention are prepared by reacting an N-hydroxy-4-trihalomethyl-6-oxatetrahydro-1,3-oxazine (II) with an isocyanate (III) as depicted in the following reaction.

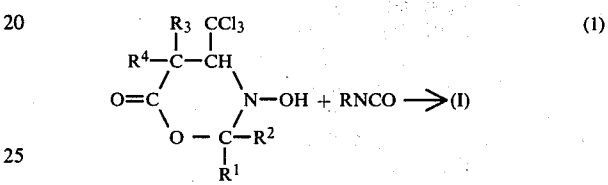

wherein

R, $R^1$, $R^2$, $R^3$ and $R^4$ have the same significance as previously defined.

Reaction (1) is conducted by conventional procedures, preferably in the presence of a catalytic amount of an organic base such as a trialkylamide. The reactants (II) and (III) are generally contacted in substantially equimolar amounts in an inert organic solvent at a temperature of 0° to 100° C., preferably 20° to 50° C. Suitable inert organic solvents include haloalkanes such as dichloromethane and aromatic compounds such as benzene and chlorobenzene. The product (I) is isolated and purified by conventional procedures such as extraction, chromatography, crystallization, etc.

FUNTICIDAL UTILITY

The compounds of the invention are useful for controlling fungi, particularly plant fungal infections caused by *botrytis cinerea*, leaf blights caused by organisms such as *Phytophthora infestans* and *Septoria apii*, downy mildew dieases caused by fungal species of the *Peronosporacea* family such as *Plasmopara viticola* and *Bremia lactucae*, and crown and root rot diseases caused by *Phytophthora* fungi such as *P. cactorum* and *P. cryptogea*. However, some fungicidal compounds of the invention may be more fungicidally active than others against particular fungi.

When used as fungicides, the compounds of the invention are applied in fungicidally effective amounts to fungi and/or their habitates, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsified concentrates, as solutions, or as any of several othr known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts, alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtues of the active fungicide with finely divided solids such as talc, natural clays, kieselguhr, pyrophyllite, chalk, diatomaceous earths, calcium phosphates, calcium and magnesium carbonates, sulfur, lime, flours and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersants, and may consist entirely of the fungicide with a liquid or solid emulsifying agent, or may also contain a liquid carrier such as xylene, heavy aromatic naphthas, isophorone, and other non-volatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphtalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier may also be used. All of those techniques for formulating and applying fungicides are well known in the art.

The percentages by weight of the fungicides may vary according to the manner in which the composition is to be applied and the particular type of formulation, but in general comprise 0.5 to 95% of the toxicant by weight of the fungicidal composition.

EXAMPLES

Example 1—Preparation of N-hydroxy-2-methyl-2-phenyl-4-trichloromethyl-5,5-dichloro-6-oxotetrahydro-1,3-oxazone A 16.2-g (0.12 mol) sample of acetophenone oxime was added to a stirred solution of 31 g (0.12mol) alpha,alphadichloro-beta-trichloromethyl-beta-propiolactone in 45 ml chlorobenzene. A moderate exotherm ensued and solids formed almost immediately. The reaction mixture was stirred at about 25° C. for 3½ hours, cooled to about 10–15° C. and filtered. The filter cake was washed with chlorobenzene, hexane, and dried to give 35 g of product, m.p. 165–169° C.

Example 2—Preparation of N-(phenylcarbamyloxy)-2-methyl-2-phenyl-4-trichloromethyl-5,5-dichloro-6-oxotetrahydro-1,3-oxazine A solution of 8 g (0.02 mol) N-hydroxy-2-methyl-2-phenyl-4-trichloromethyl-5,5-dichloro-6-oxotetrahydro-1,3-oxazine, 2.4 g (0.02 mol) phenylisocyanate and several drops triethylamine in 90 ml dichloromethane was stirred at about 10° C. for about 2 days. The reaction mixture was filtered and the filtrate was evaporated under reduced pressure to give a yellow oil. The oil crystallized from ethanol/hexane to give 4 g of product, m.p. 154°–157° C. The product is tabulated in Table I as Compound No. 8.

Other compounds of the invention were prepared by procedures similar to those of Examples 1–2. These compounds are tabulated in Table I. The structures of the compounds tabulated in Table I were verified by infrared spectroscopy and/or nuclear magnetic resonance analysis.

TABLE I

Compounds of the formula

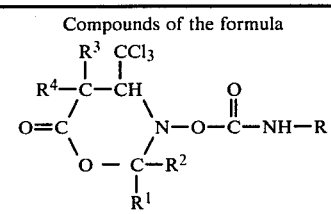

| No. | R¹ | R² | R³ | R⁴ | R | m.p., °C. | Chlorine Analysis Calc. | Found |
|---|---|---|---|---|---|---|---|---|
| 1 | $CH_3$ | $CH_3$ | H | H | φ | 91–97 | 27.9 | 29.9 |
| 2 | $CH_3$ | $CH_3$ | H | H | 2-F-φ | oil | 26.6 | 28.8 |
| 3 | —$(CH_2)_5$— | | H | H | φ | 154–157 | 25.2 | 27.7 |
| 4 | $CH_3$ | $CH_3$ | H | H | 3,4-$Cl_2$-φ | oil | 39.4 | 37.1 |
| 5 | —$(CH_2)_5$— | | H | H | 3,4-$Cl_2$-φ | 155–159 | 36.1 | 39.2 |
| 6 | $CH_3$ | $CH_3$ | H | H | φ | 209–211 | 39.4 | 39.5 |

TABLE I-continued

Compounds of the formula $$R^4-\underset{|}{C}-\underset{|}{CH}$$
with $R^3$, $CCl_3$ substituents, structure containing $O=C$, $O-C-R^2$ (with $R^1$), $N-O-C(=O)-NH-R$

| No. | $R^1$ | $R^2$ | $R^3$ | $R^4$ | R | m.p., °C | Chlorine Analysis Calc. | Chlorine Analysis Found |
|---|---|---|---|---|---|---|---|---|
| 7 | CH₃ | CH₃ | Cl | Cl | 3,4-Cl₂φ | 177–181 | 47.8 | 45.7 |
| 8 | φ | CH₃ | Cl | Cl | φ | 154–157 | 34.6 | 42.0 |
| 9 | φ | CH₃ | Cl | Cl | 3,4-Cl₂-φ | 137–140 | 42.7 | 41.9 |
| 10 | CH₃ | CH₃ | Cl | Cl | 3-Cl-φ | 166–168 | 43.9 | 51.1 |
| 11 | —(CH₂)₄— | | Cl | Cl | 4-Cl-φ | 140–144 | 41.6 | 40.6 |
| 12 | —(CH₂)₄— | | Cl | Cl | 3-Cl-φ | 127–130 | 41.6 | 36.8 |
| 13 | φ | CH₃ | Cl | Cl | 3-Cl-φ | 113–117 | 38.9 | 38.9 |
| 14 | CH₃ | CH₃ | Cl | Cl | 4-Cl-φ | 180–182 | 43.9 | 45.2 |
| 15 | φ | φ | Cl | Cl | 3-Cl-φ | 150–153 | 34.9 | 33.4 |
| 16 | φ | φ | Cl | Cl | 4-Cl-φ | 140–144 | 34.9 | 31.9 |
| 17 | —(CH₂)₄— | | Cl | Cl | 3-Cl-φ | 149–152 | 45.5 | 45.0 |
| 18 | CH₃ | CH₃ | Cl | Cl | 4-CH₃O-φ | 159–162 | 36.9 | 33.6 |
| 19 | CH₃ | CH₃ | H | H | 3,5-Cl₂-φ | 118–120 | 34.1 | 35.3 |
| 20 | CH₃ | CH₃ | H | H | 3,5-Cl₂φ | 148–152 | 39.3 | 38.8 |
| 21 | CH₃ | CH₃ | Cl | Cl | 2,6-(CH₃)₂-φ | 165–167 | 37.0 | 37.1 |
| 22 | CH₃ | CH₃ | Cl | Cl | 3-CH₃-φ | 143–147 | 38.2 | 37.2 |
| 23 | CH₃ | CH₃ | Cl | Cl | CH₃ | oil | 45.6 | 41.3 |
| 24 | CH₃ | CH₃ | H | H | 4-Cl-φ | 120–123 | 34.1 | 35.6 |
| 25 | CH₃ | n-C₃H₇ | Cl | Cl | φ | 130–132 | 37.0 | 35.6 |
| 26 | CH₃ | n-C₃H₇ | H | H | 3,4-Cl₂-φ | 138–141 | 37.0 | 38.2 |
| 27 | CH₃ | i-C₃H₇ | Cl | Cl | φ | 114–117 | 37.0 | 36.9 |
| 28 | CH₃ | i-C₃H₇ | H | H | 3,4-Cl₂-φ | 166–170 | 37.0 | 38.2 |
| 29 | C₂H₅ | C₂H₅ | Cl | Cl | φ | 147–149 | 37.0 | 37.7 |
| 30 | C₂H₅ | C₂H₅ | Cl | Cl | 3,4-Cl₂-φ | 127–130 | 37.0 | 37.0 |
| 31 | CH₃ | C₂H₅ | H | H | 4-Cl-φ | 126–128 | 33.0 | 34.4 |
| 32 | CH₃ | i-C₃H₇ | H | H | 4-Cl-φ | 119–123 | 31.9 | 36.5 |
| 33 | CH₃ | CH₃ | H | H | 4-CH₃-φ | 128–129 | 26.9 | 27.3 |
| 34 | CH₃ | CH₃ | H | H | 4-CH₃S-φ | 113–117 | 24.9 | 24.3 |

φ represents phenyl

EXAMPLE 3—Tomato Late Blight

Compounds of the invention were tested for the control of the Tomato Late Blight organism *Phytophthora infestans*. Five-to six-week-old tomato (variety Bonny Best) seedlings were used. The tomato plants were sprayed with a 250-ppm solution of the test compound in acetone, water and a small amount of a non-ionic emulsifier. The sprayed plants were then inoculated one day later with the organism, placed in an environmental chamber and incubated at 18°–20° C. and 100% relative humidity for a least 16 hours. Following the incubation, the plants were allowed to dry and then were maintained at 60–80% relative humidity for approximately 7 days. The percent disease control provided by a given test compound was based on the percent disease reduction relative to untreated check plants. The compounds giving effective control at the test concentration are tabulated in Table II.

TABLE II

Tomato Late Blight Control

| Compound No. | % Control |
|---|---|
| 4 | 96 |
| 5 | 56 |
| 6 | 98 |
| 7 | 21 |
| 8 | 97 |
| 9 | 89 |
| 10 | 68 |
| 11 | 94 |
| 12 | 68 |
| 13 | 89 |
| 18 | 95 |
| 19 | 68 |
| 21 | 88 |
| 27 | 92 |
| 28 | 23 |
| 30 | 63 |
| 31 | 27 |
| 32 | 56 |
| 33 | 21 |

Example 4—Powdery Mildew

The powdery mildew test was made using bean seedlings (cultivar Bountiful) with well-developed primary leaves. The pathogen was *Ersiphe polygoni*. The bean seedlings were sprayed with a 250-ppm solution of the test compound in an acetone-water mixture containing a non-ionic emulsifier. The treated plants were inoculated one day after spray application of the test compound with the pathogen. The plants were then maintained in a greenhouse at 60–80% relative humidity and at a temperature of 20°–22° C. The rate of infection on the leaves were checked after about 10 days. The percent disease control provided by a given test compound was based on the disease reduction relative to untreated check plants. The compounds of the invention giving effective control at the test concentration are reported in Table III.

TABLE III

Powdery Mildew Control

| Compound No. | % Control |
| --- | --- |
| 1 | 91 |
| 2 | 75 |
| 15 | 11 |
| 19 | 97 |
| 24 | 75 |
| 30 | 93 |
| 32 | 100 |
| 33 | 96 |

Example 5—Tomato Early Blight

Compounds of the invention were tested for the control of the Tomato Early Blight organism, *Alternaria solani*. Tomato (cultivar Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants. The compounds giving effective control at the test concentration are tabulated in Table IV.

TABLE IV

Tomato Early Blight Control

| Compound No. | % Control |
| --- | --- |
| 1 | 21 |
| 2 | 21 |
| 6 | 64 |
| 7 | 18 |
| 8 | 84 |
| 10 | 84 |
| 11 | 84 |
| 12 | 33 |
| 14 | 27 |
| 15 | 51 |
| 16 | 68 |
| 17 | 33 |
| 31 | 39 |
| 32 | 23 |

Example 6—Celery Late Blight

Compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a non-ionic emulsifier. The plants were then inoculated with the organism and placed in an environmental chamber and incubated at 1820–20° C. in 100% relative humidity for an extended period of time (approximately 48 hours). Following the incubation, the plants were allowed to dry and then were maintained at 60–80% relative humidity for approximately 14 days. The percent disease control provided by a given candidate toxicant is based on the percent disease reduction relative to untreated check plants. The compounds giving effective control at the test concentrations are reported in Table V.

TABLE V

Celery Late Blight Control

| Compound No. | % Control |
| --- | --- |
| 8 | 61 |
| 11 | 42 |
| 31 | 64 |

Example 7—Botrytis cinerea control

Compounds Nos. 1, 8 and 11 were tested as preventive fungicides against *Botrytis cinerea* on harvested mature grape berries (cultivar Emperor) by the following procedure: 4 grape bunches (trimmed to approximately 50 berries) were sprayed with a 250-ppm solution of the test compound in a solution of water, acetone and a small amount of a non-ionic emulsifier. The sprayed grapes were inoculated approximately one day later with 2- to 3-week-old spores of *Botrytis cinerea* grown on potato dextrose agar plants. The rate of disease incidence was determined 6–9 days after inoculation, when disease symptoms are fully evident on non-treated check grapes. Infection is determined by actual count of the number of infected berries. The percent disease control provided by a test compound was calculated from the percentage disease reduction based on the non-treated check plants. The test compound and results are tabulated in Table VI.

TABLE VI

*Botrytis cinerea* control

| Compound No. | % Control |
| --- | --- |
| 1 | 23 |
| 8 | 100 |
| 11 | 78 |

Example 8—Preventive Grape Downy Mildew Control

Compounds Nos. 1, 4, 13 and 19 were tested for the control of the grape downy mildew organism *Plasmopara viticola*. Detached leaves, between 70 and 85 mm in diameter, of 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environmental chamber and incubated at 18°–22° C. and about 100% relative humidity. Seven to nine days after inoculation, the amount of disease control was determined. The percent disease control provided by a given test compound was based on the percent disease reduction relative to untreated check plants. The test compounds, test concentrations and results are tabulated in Table VIII.

TABLE VII

Grape Downy Mildew Control

| Compound No. | Conc. | % Control |
| --- | --- | --- |
| 1 | 250 ppm | 23 |
| 4 | 100 ppm | 60 |
| 13 | 100 ppm | 73 |
| 19 | 100 ppm | 78 |

What is claimed is:

1. A compound of the formula

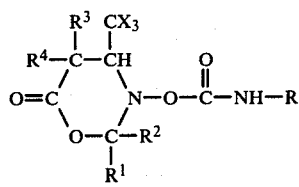

wherein
- $R^1$ and $R^2$ individually are alkyl of 1 to 6 carbon atoms, phenyl, or phenyl substituted with 1 to 3 of the same or different substituents selected from fluoro, chloro, bromo, iodo, alkyl of 1 to 4 carbon atoms, alkoxy of 1 to 4 carbon atoms or alkylthio of 1 to 6 carbon atoms,
- X is chloro or bromo,
- $R^3$ and $R^4$ individually are hydrogen, chloro, bromo or alkyl of 1 to 6 carbon atoms,
- R is hydrogen, alkyl of 1 to 6 carbon atoms, phenyl, or pheny substituted with 1 to 3 of the same or different substituents selected from fluoro, chloro, bromo, iodo, alkyl of 1 to 4 carbon atoms, alkoxy of 1 to 4 carbon atoms or alkylthio of 1 to 6 carbon atoms, with the proviso that two $R^1$ and $R^2$ groups may together form a divalent alkylene group of 3 to 5 carbon atoms.

2. The compound of claim 1 wherein R is phenyl or phenyl substituted with 1 to 2 of the same or different substituents selected from fluoro, chloro, bromo, alkyl of 1 to 4 carbon atoms or alkoxy or 1 to 4 carbon atoms.

3. The compound of claim 1 wherein R is phenyl or phenyl substituted with 1 to 2 fluoro, chloro or bromo.

4. The compound of claim 3 wherein $R^1$ and $R^2$ are alkyl.

5. The compound of claim 3 wherein $R^1$ is alkyl and $R^2$ is phenyl or phenyl substituted with 1 to 2 of the same or different substituents selected from fluoro, chloro, bromo, alkyl of 1 to 4 carbon atoms or alkoxy of 1 to 4 carbon atoms.

6. The compound of claim 3 wherein $R^1$ and $R^2$ together form trimethylene or tetramethylene.

7. The compound of claim 3 wherein $R^3$ and $R^4$ are hydrogen, chloro or bromo.

8. The compound of claim 3 wherein $R^1$ is alkyl, $R^2$ is phenyl or phenyl substituted with 1 to 2 fluoro, chloro or bromo, X is chloro, $R^3$ and $R^4$ are chloro.

9. The compound of claim 3 wherein $R^1$ and $R^2$ are methyl, X is chloro, $R^3$ and $R^4$ are chloro and R is phenyl.

10. A method for the control of plant fungi which comprises applying to said fungi or their plant hosts a fungicidally effective amount of the compound defined in claim 1.

11. A fungicidal composition comprising a biologically inert carrier and a fungicidally effective amount of the compound defined in claim 1.

* * * * *

UNITED STATES PATENT AND TRADEMARK OFFICE
CERTIFICATE OF CORRECTION

PATENT NO. : 4,151,279
DATED : April 24, 1979
INVENTOR(S) : Malcolm S. Singer

It is certified that error appears in the above-identified patent and that said Letters Patent are hereby corrected as shown below:

Column 1, line 12 "of oximes" should read --or oximes--.

Column 2, line 11, "triemthylene" should read --trimethylene--.

Column 2, line 33, "trialkylamide" should read --trialkylamine--.

Column 2, line 48, "dieases" should read --diseases--.

Column 3, line 2, "emulsified" should read --emulsifiable--.

Column 4, line 12, "fungicides" should read --fungicide--.

Column 4, line 21, "oxazone" should read --oxazine--.

Column 4, line 41, "oil" should read --oil was--.

Column 6, line 63, "were" should read --was--.

Column 7, line 41, "39" should read --79--.

UNITED STATES PATENT AND TRADEMARK OFFICE
CERTIFICATE OF CORRECTION

PATENT NO. : 4,151,279

DATED : April 24, 1979

INVENTOR(S) : Malcolm S. Singer

It is certified that error appears in the above—identified patent and that said Letters Patent are hereby corrected as shown below:

Column 7, line 54, "1820-20°C" should read --18-20°C--.

Column 8, line 27, "plants" should read --grapes--.

Signed and Sealed this

Eighth Day of January 1980

[SEAL]

Attest:

SIDNEY A. DIAMOND

*Attesting Officer*   *Commissioner of Patents and Trademarks*